United States Patent
Burns et al.

(10) Patent No.: US 10,481,059 B2
(45) Date of Patent: Nov. 19, 2019

(54) SYSTEM AND METHOD FOR REMOTE MONITORING OF SOLID CONTAMINANT IN FLUIDS

(71) Applicants: Jack D. Burns, Mineral Wells, TX (US); Stephen G. Jeane, Mineral Wells, TX (US); Jeremy M. Stevens, Fort Worth, TX (US)

(72) Inventors: Jack D. Burns, Mineral Wells, TX (US); Stephen G. Jeane, Mineral Wells, TX (US); Jeremy M. Stevens, Fort Worth, TX (US)

(73) Assignee: Parker Hannifin Filtration (US), Inc., Mineral Wells, TX (US)

( * ) Notice: Subject to any disclaimer, the term of this patent is extended or adjusted under 35 U.S.C. 154(b) by 338 days.

(21) Appl. No.: 15/260,087

(22) Filed: Sep. 8, 2016

(65) Prior Publication Data

US 2018/0067032 A1 Mar. 8, 2018

(51) Int. Cl.
*G01N 7/10* (2006.01)
*G01N 15/06* (2006.01)
*G01N 15/00* (2006.01)

(52) U.S. Cl.
CPC .......... *G01N 7/10* (2013.01); *G01N 15/0618* (2013.01); *G01N 2015/0046* (2013.01)

(58) Field of Classification Search
CPC .............................. G01N 7/10; G01N 15/0618
See application file for complete search history.

(56) References Cited

U.S. PATENT DOCUMENTS

| 4,690,698 | A  | * | 9/1987  | Reid ................... B01D 47/025 95/200 |
| 6,705,161 | B1 | * | 3/2004  | Klassen ................ F01C 3/085 73/261 |
| 7,854,158 | B2 |   | 12/2010 | Burns et al. |
| 7,948,621 | B2 |   | 5/2011  | Burns et al. |
| 2005/0151968 | A1 |   | 7/2005  | Drake et al. |
| 2007/0256983 | A1 |   | 11/2007 | Hinckley et al. |
| 2011/0094296 | A1 |   | 4/2011  | Burns et al. |
| 2015/0037208 | A1 | * | 2/2015  | Witt ...................... B01J 19/087 422/28 |

(Continued)

FOREIGN PATENT DOCUMENTS

| CN | 102778537 A | 11/2012 |
| WO | WO 2009/002322 A1 | 12/2008 |

OTHER PUBLICATIONS

Babich et al., Development and Evaluation of a Continuous Ambient PM2.5 Mass Monitor, Apr. 2000, Aerosol Science and Technology 32:309-324 (Year: 2000).*

*Primary Examiner* — David Z Huang
(74) *Attorney, Agent, or Firm* — Reinhart Boerner Van Deuren P.C.

(57) ABSTRACT

A pipeline contaminant monitoring apparatus that includes a filter housing and probe configured to isokinetically sample a portion of a pipeline gas stream. The filter housing has a filter configured to trap solid contaminants within the gas stream. A first pressure sensor is located upstream of the filter and a second pressure sensor is located downstream of the filter. A processor is coupled to the first and second pressure sensors. The processor is configured to determine a solid contaminant concentration level in the gas stream based on a rate of change of the pressure drop sensed across the filter.

14 Claims, 5 Drawing Sheets

(56) References Cited

U.S. PATENT DOCUMENTS

2015/0367270 A1* 12/2015 Mazumder ......... B01D 46/0001
96/226
2017/0101916 A1* 4/2017 Klaas ..................... F01N 9/002

* cited by examiner

SYSTEM AND METHOD FOR REMOTE MONITORING OF SOLID CONTAMINANT IN FLUIDS

FIELD OF THE INVENTION

The invention generally relates to a contaminant monitoring system and method for use in pipelines, such as those carrying hydrocarbon gases.

BACKGROUND OF THE INVENTION

Dry black powder contaminant poses an operational risk with respect to pipelines. Particles of dry black powder become entrained in the gas and should be removed to maintain pipeline and instrument integrity. Black powder is a mixture of pipeline corrosion products consisting of iron oxides, iron sulfides, iron carbonates, and other solid contaminant. When solid contaminant, such as black powder, reaches a sufficiently high concentration, the devices that use the hydrocarbon gas may be adversely affected. Black powder will plug power plant fuel injection nozzles and furnace burner tips causing equipment damage and potentially an increase in the plant's environmentally regulated emissions.

A number of pipeline contaminant monitoring devices have been developed and tested. Most have had operational issues, due to contaminant build up or scaling on measurement sensors. For example, PECOFacet's PlantGard™ laser particle counting contaminant monitor uses a sapphire laser optical tube to keep sampled gas separated from electrical laser components. Laser light is beamed through the optical tube to reach the gas stream and the particles carried within. When sampling dry solid particulate, a static build up will occur on non-conductive laser optical structures and lens. The static charge that builds up will attract dry solid particles and cause them to stick to optical surfaces. Once optical surfaces build up with solids, laser light is deflected creating false positive particle counts inflating particle count values. Most contaminant sensing devices will suffer from this issue or other like contaminant coating problems.

Embodiments of the invention provide a contaminant monitoring system that addresses the problems described above. These and other advantages of the invention, along with additional inventive features, will be apparent from the description of the invention provided herein.

BRIEF SUMMARY OF THE INVENTION

In one aspect, embodiments of the invention provide a pipeline contaminant monitoring apparatus that includes a filter housing and sample probe configured to isokinetically sample a portion of a pipeline gas stream. The filter housing has a filter designed to trap solid contaminants located in the sample stream. A first pressure sensor is located upstream of the filter and a second pressure sensor is located downstream of the filter. A processor is coupled to the first and second pressure sensors to measure the differential pressure drop. The processor is configured to determine a solid contaminant concentration level in the gas stream based on a rate of change of the differential pressure drop measured across the filter.

In a particular embodiment, the pipeline contaminant monitoring apparatus includes a remote transmitting unit configured to transmit data signals to the processor. The processor may be remotely located from the first and second pressure sensors. In certain embodiments, the remote transmitting unit is configured to wirelessly transmit data signals to the processor.

In a further embodiment, the processor is configured to compare the pressure drop measured across the filter housing, to empirically-derived laboratory data, so that the contaminant concentration in the pipeline can be calculated. In some embodiments, the sampling probe is positioned to capture a representative sample of contaminant in the pipeline and is set to an isokinetic flow rate from the pipeline to the filter housing. Embodiments of the pipeline contaminant monitoring apparatus further include a liquid collection chamber attached to a gravitational bottom of the filter housing, where the liquid collection chamber is positioned to collect liquid droplets from the filter. The liquid collection chamber includes a float switch configured to generate an electrical signal when a predefined amount of liquid is collected in the liquid collection chamber. The processor is configured to determine a level of liquid contaminant concentration in the gas stream based on a time required for the float switch to generate the electrical signal.

In some embodiments, the processor is configured to generate an alarm if the solid or liquid contaminant concentration level is higher than a predetermined threshold. In certain embodiments, the pipeline contaminant monitoring apparatus has a booster pump to inject sampled gas back into the pipeline gas stream.

In another aspect, embodiments of the invention provide a method of monitoring contaminant concentration in a pipeline gas stream. The method includes the steps of diverting a portion of a pipeline gas stream and directing the diverted portion of the gas stream through a filter barrier. The method calls for measuring a pressure differential across a filter barrier at a first time, and measuring the pressure differential across the filter barrier at a second time later than the first time. The method further includes determining a measured rate of pressure change for a time period from the first time to the second time. The method further includes storing empirical data for solid contaminant concentration with respect to a differential pressure rate of change across a filter medium, comparing the measured rate of pressure change to the empirical data, and determining a solid contaminant concentration level based on the comparison.

In a particular embodiment, the method also includes collecting, from the filter barrier, liquid contaminants in a collection chamber, determining a time for collecting a predefined amount of liquid contaminants in the collection chamber, and determining a liquid contaminant concentration level in the pipeline gas stream based on the time required to collect the predefined amount of liquid contaminants. In a further embodiment, the method includes displaying the contaminant concentration level on an electronic display. In certain embodiments, the method calls for transmitting pressure differential data to a remotely-located processor that determines the measured rate of pressure change, stores the empirical data, and compares the measured rate of pressure change to the empirical data.

In a particular embodiment, diverting a portion of the pipeline gas stream includes inserting a probe into the pipeline, where the probe is configured to capture a representative sample of contaminant from the gas stream, set at an isokinetic flowrate, so that an accurate assessment of contaminant can be measured.

In other embodiments of the method, determining a solid contaminant concentration level requires scaling the empirical data to account for an inner diameter of the pipeline, and using the time period to determine the solid contaminant concentration level for a standard gas flowrate through the pipeline. Certain embodiments of the invention include non-isokinetic sampling of the gas stream.

Embodiments of the method include the step of injecting the diverted portion of the gas stream back into the pipeline. Further embodiments of the method include generating an alarm if the solid or liquid contaminant concentration level is higher than a threshold level.

In another aspect, embodiments of the invention provide a method of determining contaminant load in a pipeline. The method includes isokinetic sampling of a sample portion of a gas stream through the pipeline, filtering the sample portion through a filter arranged along the pipeline, and determining a contaminant load based upon the filtering.

In a particular embodiment, the portion comprises between 0.0000019% and 0.0000021% of the flow through the pipeline. In this embodiment, the gas stream is primarily hydrocarbon gas having liquid and solid contaminants therein, and the filtering includes trapping solid contaminants in the filter and separating liquid contaminants into a collection vessel. In certain embodiments, the method calls for sensing a pressure drop across the filter, where the filter has an initial pressure drop and solid contaminants load into the filter increasing the pressure drop.

In another embodiment, the method calls for sampling a portion of a gas stream the portion comprises $6.4 \times 10^{-9}$ square feet for a 60-inch diameter pipeline, using a ¼ inch sampling probe, and wherein the gas stream comprises primarily hydrocarbon gas having liquid and solid contaminants The method may further call for using a processor to automatically determine a level of solid contaminant in the gas stream based upon a sensed pressure drop. This is done by referencing a known mass of solids from empirical testing and scaling the lab tested mass of solids to solids in the pipeline vs. time. In some embodiments, the filter collects liquid contaminants in a collection vessel for measurement, and further comprising measuring and recording a liquid contaminant level versus time.

Embodiments of the method require recording the pressure drop at predetermined intervals, where the processor determines a level of solid contaminants in the gas stream based upon a rate of change of the sensed pressure drop in comparison to pressure drop versus time data for a predetermined baseline constant contaminant loading of the filter. In some embodiments, the method calls for servicing and replacing the filter at regular intervals between 10 days and 90 days. Embodiments of the method include returning the sample portion of the gas stream to the pipeline. Further, the method may include sampling and returning the gas on a continuous basis via inlet and outlet plumbing fluidically connecting the pipeline and the filter.

Further embodiments of the invention call for recording a series of pressure differential points such that, over time, the pressure differential points form a trend line. The method may also include using the slope value of the trend line to compare stored empirical data to current recorded data in order to determine if current solid contaminant levels are more than typical base-line values. If the current solid contaminant levels are more than typical base-line values, an alarm may be automatically triggered. The alarm may be audible, visual, or some type of electronic message transmitted to the end user.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Figure 1:
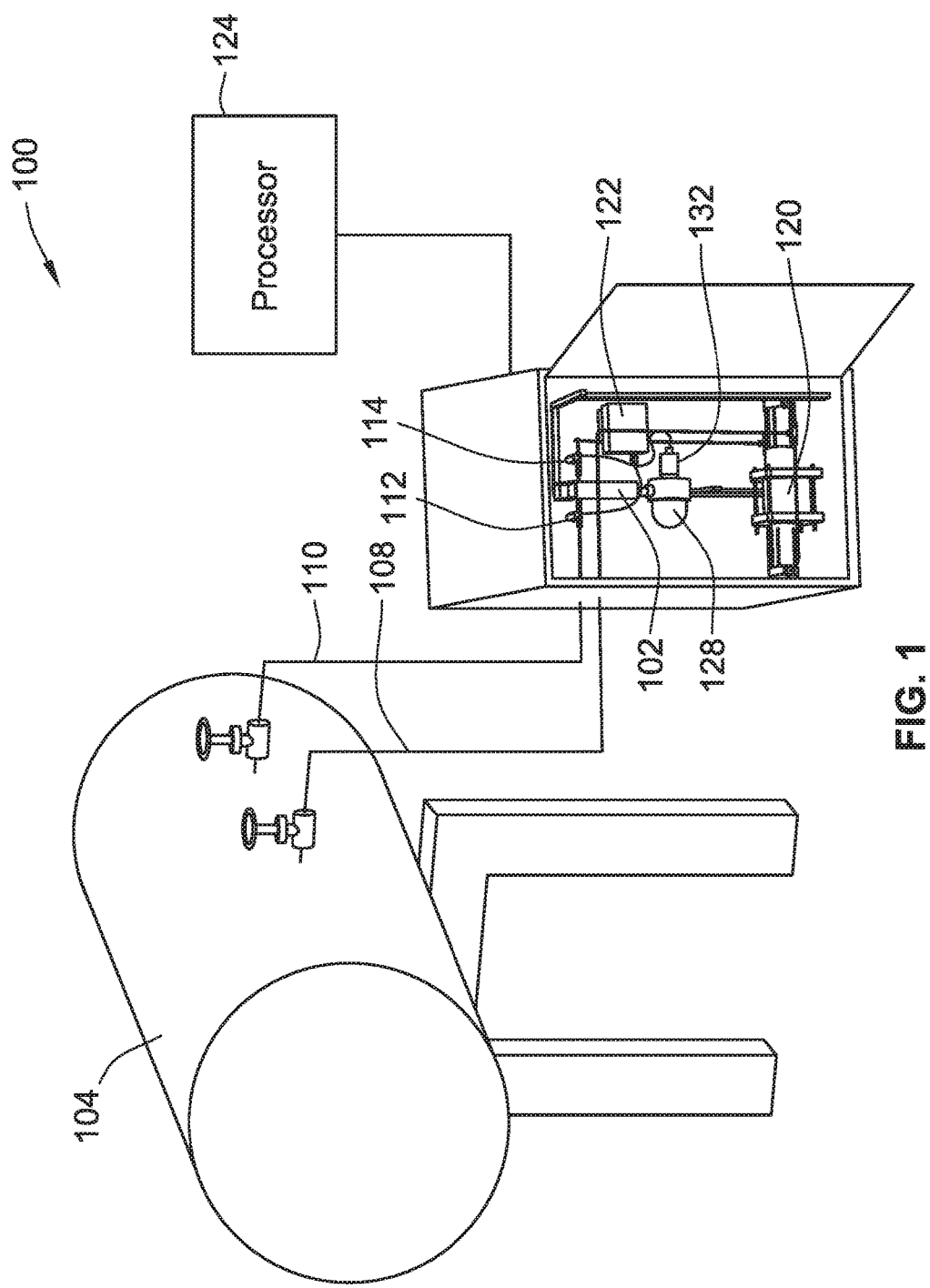
FIG. 1 is a perspective view of a contaminant concentration monitoring apparatus, constructed in accordance with an embodiment of the invention.
Figure 2:
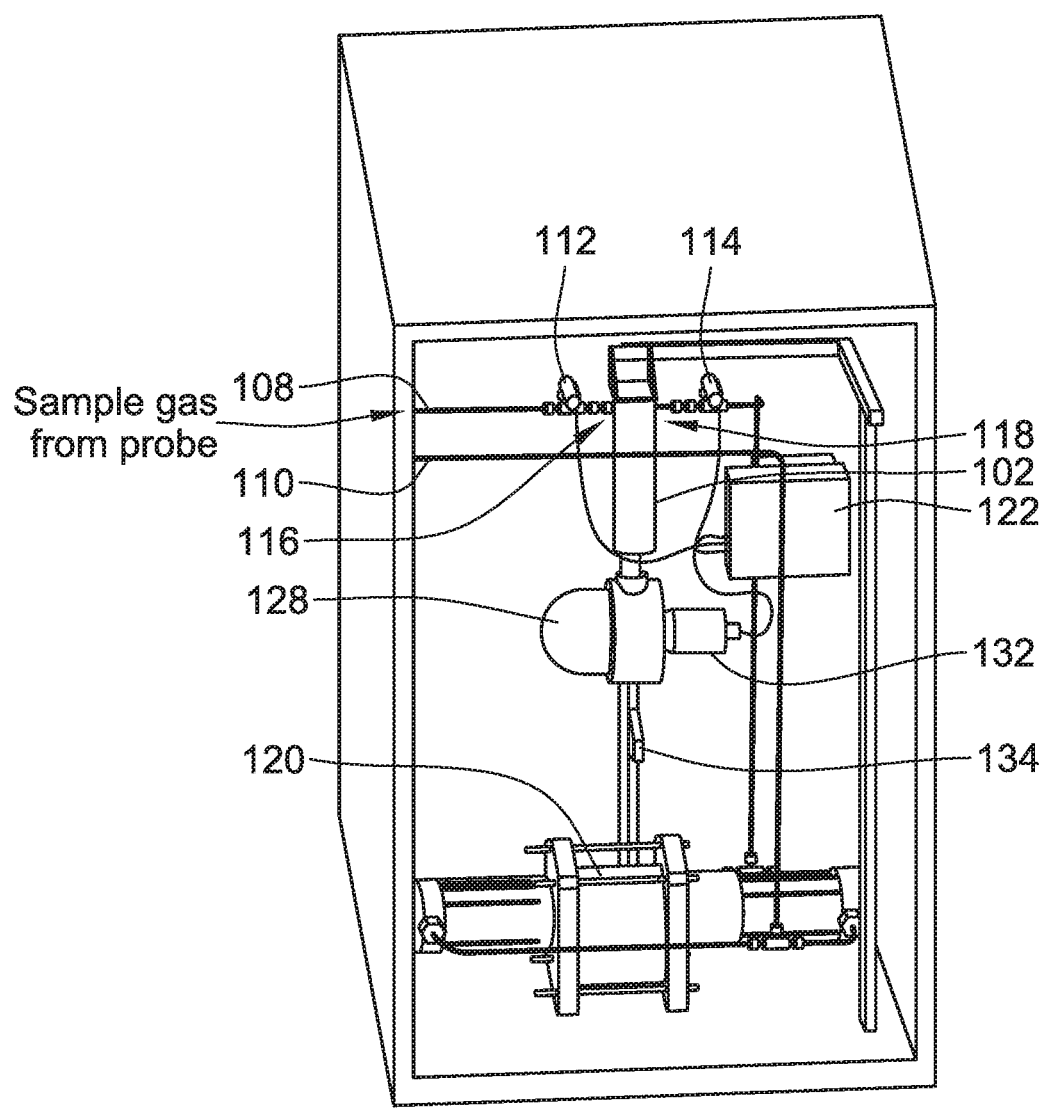
FIG. 2 is a close up perspective view of a portion of the contaminant concentration monitoring apparatus shown in claim 1.

FIGS. 1 and 2 show perspective views of a pipeline contaminant monitoring apparatus 100 according to an embodiment of the invention. The pipeline contaminant monitoring apparatus 100 is designed to actively monitor a contaminant concentration level for any closed loop, natural gas system. Embodiments of the present invention teach a system and method for determining contaminant load in a pipeline. The system and method calls for the isokinetic sampling of a pipeline gas stream. The gas stream portion is filtered and a contaminant load is determined by utilizing pressure sensors 112, 114 placed in front of the inlet 116 of a filter housing 102 and after the outlet 118 of the filter housing 102. By applying an algorithm to the values sensed by the pressure sensors 112, 114, the pipeline contaminant monitoring apparatus 100 is able to monitor the contaminant concentration level in real-time. In a particular embodiment, telecommunications deliver raw pressure data and system diagnostics from a remote location to processors, or computer servers, which process the data in real time. This data can then be displayed on an electronic dashboard for the end user. In certain embodiments, the electronic dashboard can be accessed via the internet or alternate communication protocols. The data may be provided to a computer network or distributed control system (DCS) of the end user.

Figure 3:
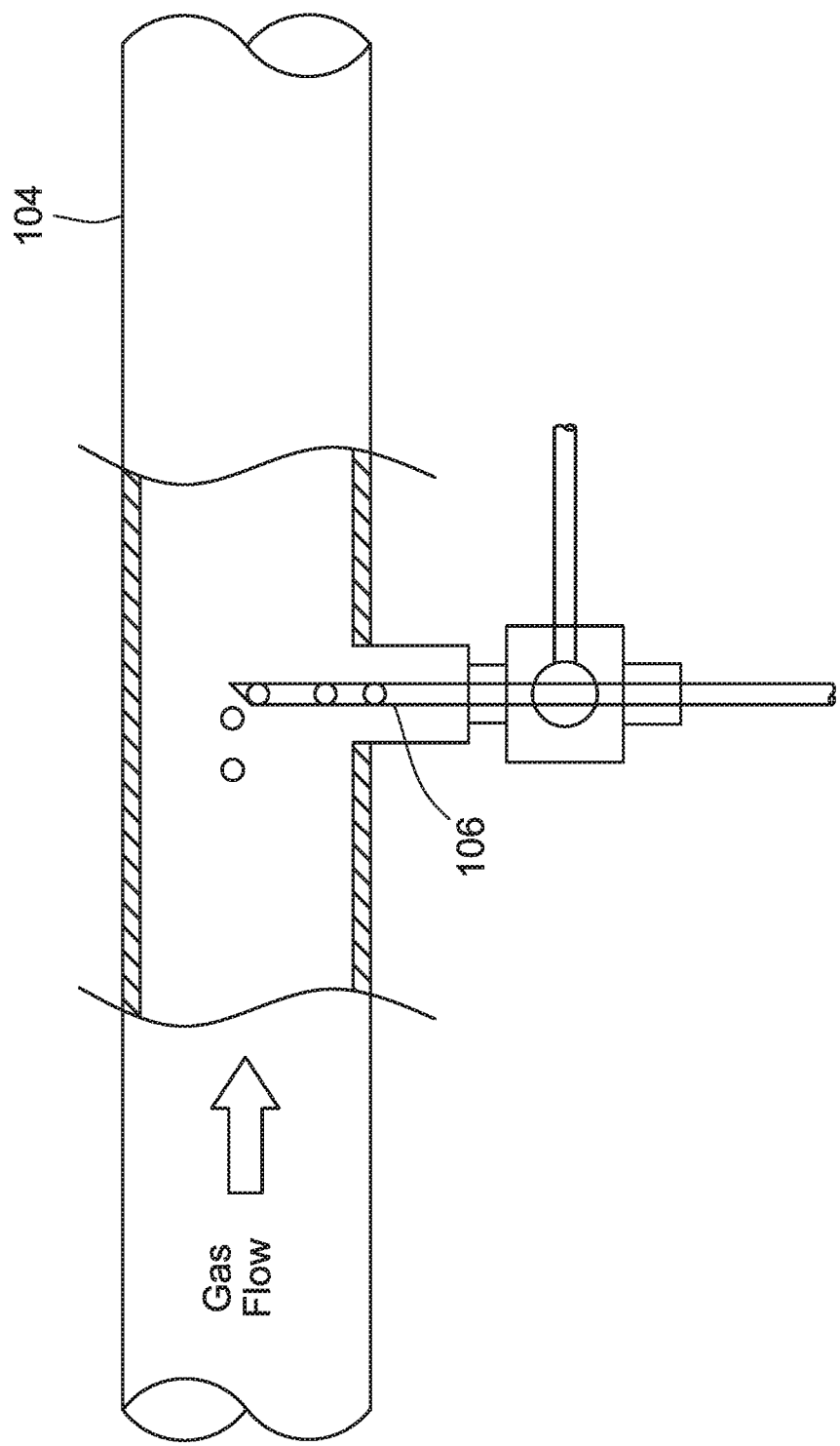
FIG. 3 is a cross-sectional view of a probe installed in a gas-carrying pipeline according to an embodiment of the invention.

The pipeline contaminant monitoring apparatus 100 includes a filter housing 102 having a filter/coalescer 103 (shown in FIG. 4) disposed therein. The filter housing 102 receives from pipeline 104 the sampled portion of the gas stream, which is acquired via the probe 106 (shown in FIG. 3) inserted into the pipeline 104. An intake line 108 runs from the probe 106 to an inlet port 116 of the filter housing 102 and delivers the sampled portion of the gas stream to the filter housing 102. A second, or return, line 110 returns the sampled portion of the gas stream from an outlet port 118 of the filter housing 102 back to the pipeline 104.

In the embodiments of FIGS. 1 and 2, a booster pump 120 is coupled between the filter housing 102 and the return line 110. After the sampled portion of the gas stream exits the filter housing 102, it will travel to the booster pump 120, which will increase the pressure of the sampled gas to a value exceeding the pipeline pressure. The boosted pressure of the sampled gas will allow the sampled gas to be re-inserted into the pipeline 104 just a few feet downstream of the sampling probe 106. The re-injection of sampled gas saves the gas and eliminates the need for burning the gas or releasing it into the atmosphere.

Referring again to FIG. 3, the location of the probe 106 on the pipeline 104 is selected to position the probe opening, inside the pipeline 104 to a position that will collect a representative sample of contaminant from the gas stream. The flowrate for the probe 106 is set to an isokinetic flowrate, given the pipeline flowrate and process conditions. In a typical embodiment of the invention, the sampling probe 106 has an outer diameter of 0.25 inches. In alternate embodiments, the outer diameter could range from 1/8 of an inch to 1/2 of an inch. Typically, the probe 106 is attached via flexible or semi-rigid tubing or a high pressure hose (i.e., intake line 108) to the inlet port 116 of the filter housing 102.

In a certain embodiment of the invention, the sampled portion of the pipeline gas stream comprises between 0.0000318% and 0.00004% for a 48-inch pipeline. In a typical embodiment, 0.0000415% of the gas will be sampled for a 42-inch diameter pipeline using the 0.25-inch diameter probe.

Figure 4:
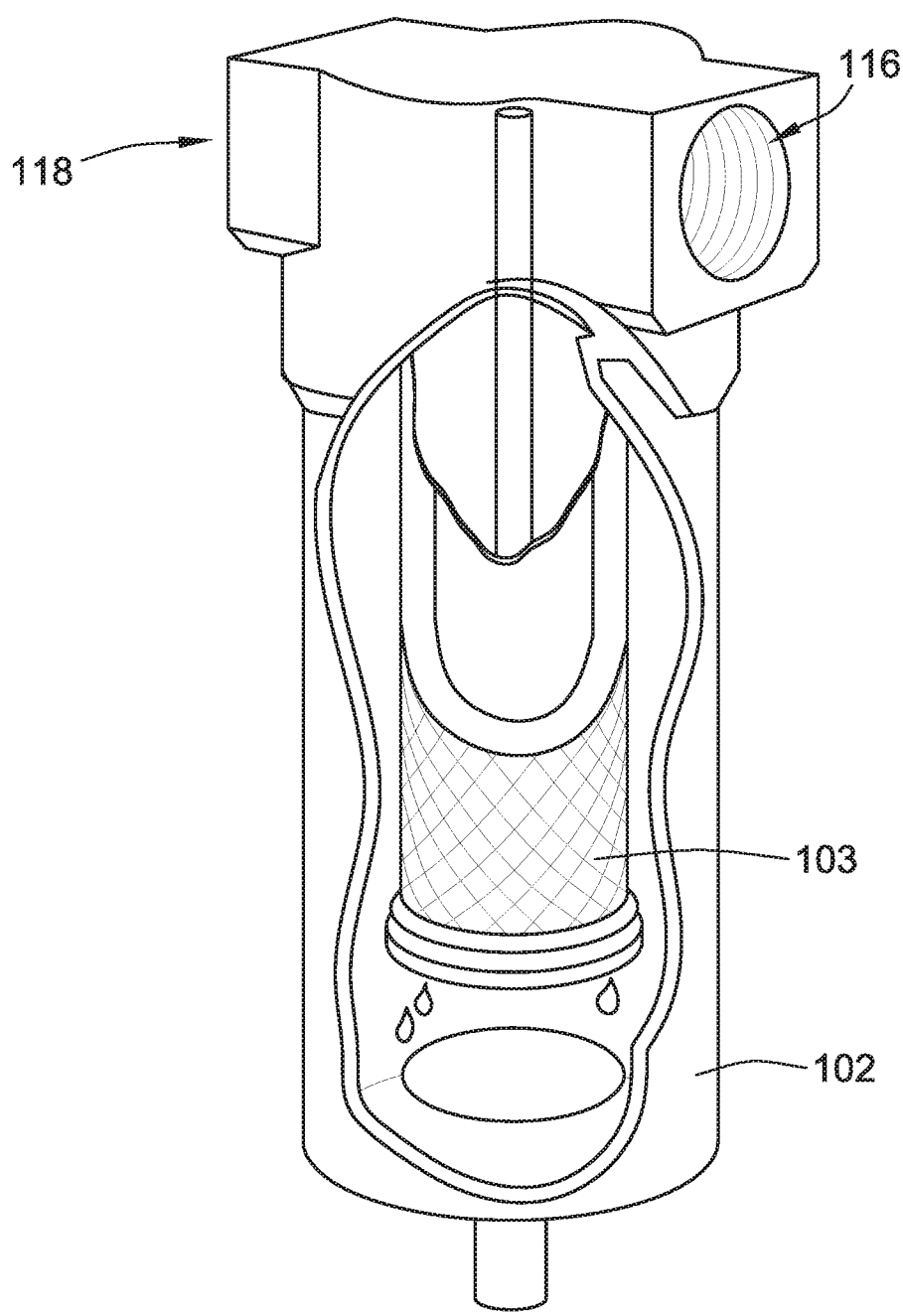
FIG. 4 is an exemplary embodiment of a filter housing with filter element.

In a more particular embodiment, the filter housing 102 will utilize a 0.1 to 1 micron gas liquid filter element. FIG. 4 illustrates an exemplary filter housing 102 with an exemplary filter element 103. The sampled portion of the gas stream will flow through the inlet port 116 to the filter housing 102 and will be directed to flow inside the filter element 103. The flow through the filter element 103 results in the filtered portion of the gas stream being outside of filter element 103. The filtered gas stream exits the filter housing 102 through outlet port 118. In the embodiment shown, the filter element 103 is cylindrically-shaped, though it is envisioned that other types of filter elements could be used in various embodiments of the invention. It is contemplated that the system may be designed such that the filter is replaced at regular intervals ranging from 10 days to 90 days.

A first pressure sensor 112 is disposed upstream of the filter and a second pressure sensor 114 is disposed downstream of the filter. In the embodiment shown in FIG. 2, the first pressure sensor 112 is positioned upstream of the filter housing 102 and a second pressure sensor 114 is positioned downstream of the filter housing 102.

A remote transmitting unit (RTU) 122 is coupled to the first and second pressure sensors 112, 114. The remote transmitting unit 122 is configured to transmit an electrical signal, typically an analog signal, from the pressure sensors 112, 114 via a cell modem, or similar communication device, to a processor 124. The RTU 122 may transmit the signal using wired or wireless means, depending on the particular embodiment.

In one embodiment, the processor 124 is a data center processing server (not shown). The processor 124 may be located in the vicinity of the contaminant monitoring apparatus 100, or may be located remotely (e.g., several thousand miles) from the contaminant monitoring apparatus 100. The processor 124 is configured to execute a unique algorithm that will perform a differential pressure rate of change calculation and compare it to empirically derived data to produce a solids concentration value for the gas stream flowing in the pipeline 104. Specifically, pressure differential measurements are taken over time, and the time required for the transition from one differential pressure point to a second differential pressure point is correlated to the mass of solid contaminants associated with same two differential pressure points in an empirical test. The empirical test data is stored in electronic memory accessible to the processor 124.

To obtain the empirical data, the rate of change for both solid and liquid contaminants is monitored for a period of time to determine normal baseline data for the pipeline gas stream when it is in a normal contaminant non-upset operation mode. In a particular embodiment, a differential pressure for solid contaminants is plotted using the aforementioned algorithm, and a trend line for pressure differential data is calculated. In a more particular embodiment, an alarm, for example a red flashing light or audible siren, will signal when the slope of the trend line is greater than the normal operation, non-upset condition, baseline trend slope, thus signaling a higher than normal contaminant concentration level. In this context, "normal" operation refers to the level of solid and liquid contaminant concentration typically found in the pipeline gas stream. Using the slope of the data trend line will normalize the data and filter out measurement high and low data points.

A filter and filter housing 102 are tested and calibrated, so that a baseline for calculations can be determined. Testing and weighing of the filter at known differential pressure points gives a known quantity of solids that can be translated to the mass of solids in the pipeline for the same pressure differential. Empirical data is generated based on measurements of the solids loading for the test filter at various predetermined pressure differentials. Pressure differential data is correlated to known masses trapped by the filter so that the mass of solids for each differential pressure point can be scaled to a mass of solids in the pipeline 104. Specifically, the mass of solids in the filter at two different differential pressures, i.e., dp1 and dp2, is measured.

The following equation indicates the mass of solid contaminants trapped by the filter during the transition for the first differential pressure point (dp1) to the second differential pressure point (dp2).

$$G_{ms(test)} = G_{ms(dp2)} - G_{ms(dp1)}$$

This information can be scaled to determine the mass of solids and the rate at which the solids are fed in the pipeline.

In operation, the probe 106 isokinetically samples a portion of the gas stream flowing in the pipeline 104, directing the gas stream to the filter in the filter housing 102 via the intake line 108. The first pressure sensor 112 and the second pressure sensor 114, together, measure a pressure differential across the filter element 103 (shown in FIG. 4). As solid contaminants are trapped by the filter and build up on the filter over time, the pressure differential across the filter element will increase.

The rate of change for the pressure differential is measured over time, and correlated to the empirical data obtained for the filter and filter housing 102. The empirical data is then scaled (as shown in the equation below) for the pipeline gas stream by multiplying the mass obtained from the empirical data times the ratio of the cross-sectional area for the inner diameter of the pipeline to the cross-sectional area for the inner diameter of the probe. The resulting product is divided by the time required for the change between the two differential pressure points.

$$\frac{Gms_{(Pipeline)}}{Minute} = Gms_{(Test)} * \frac{Pipe\ LD.SA(ft^2)}{Probe\ LD.SA(ft^2)} * \frac{1}{(X)Time_{(minutes)}}$$

The process flowrate above can be converted, as shown below, into an industry-wide standard (e.g., MMSCFD) to calculate a solid contaminant concentration level in terms of a standard flowrate, i.e., $$\frac{gms}{MMSCF},$$

as illustrated in the equation below.

$$\frac{Gms}{MMSCF} = \frac{1440\frac{(min)}{Day}}{(X)MMSCFD} * \frac{(X)gms_{Pipeline}}{Minute}$$

MMSCF = (Million Standard Cubic Feet)

Gas Flowrate = MMSCFD (Million Standard Cubic Feet per Day)

The processor is configured to display the resulting solid contamination concentration level $$\left(\text{i.e., } \frac{gms}{MMSCF}\right)$$

on a wired or wireless end user device, for example, in the form of a webpage for the end user, along with a graphical representation of the solids loading rate of change. The end user webpage could be hosted on the server of the contaminant monitoring apparatus 100, or on some other server.

Variations in the solids concentration level in the pipeline gas stream will change the timeframe for the monitoring system to reach a given set of differential pressure points, and the RTU 122 will transmit this information to the processor 124. In particular embodiments, the processor 124 processes this information and provides a web-based graphical representation to the client device of the end user. The client device could be a personal computer, electronic display, or mobile electronic device, such as a smartphone or tablet computer.

Figure 5:
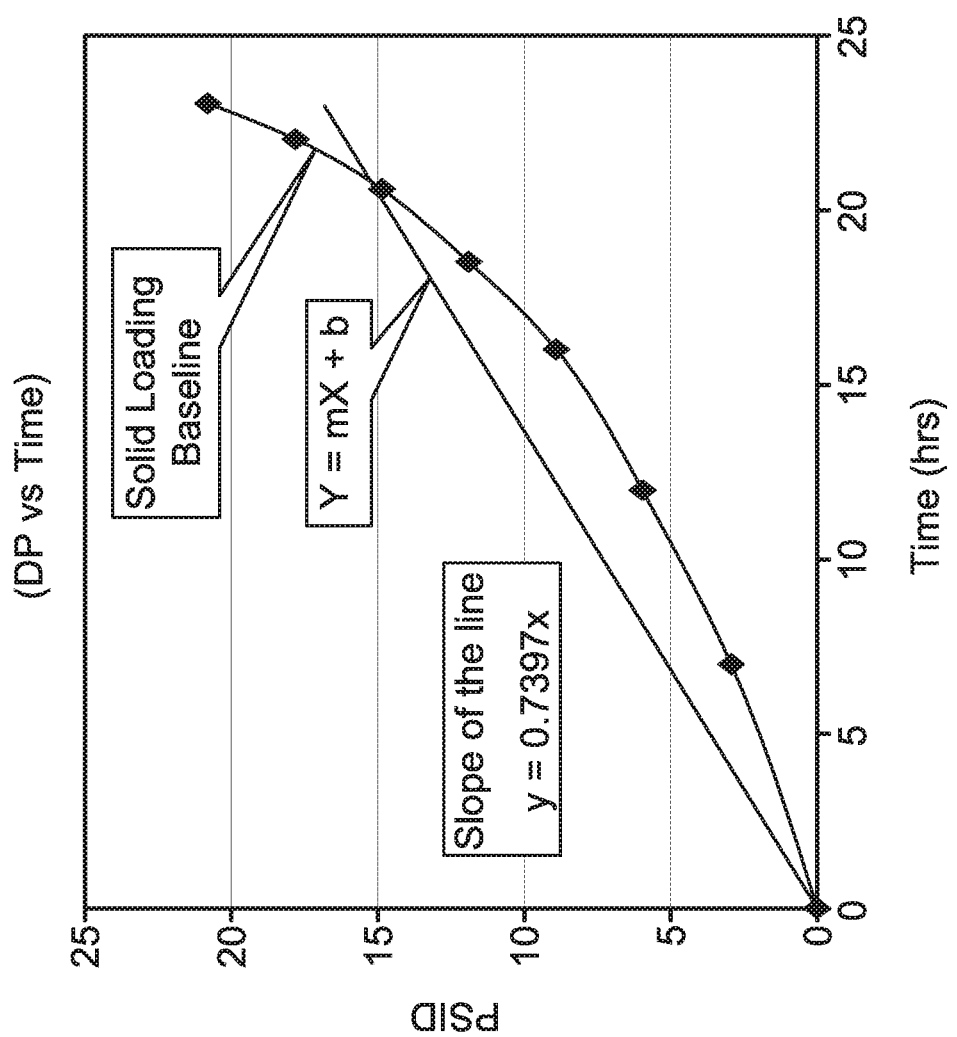
FIG. 5 is a graphical illustration of a solid contaminants loading curve for a filter.

Charting these pressure drops allows the pipeline contaminant monitoring apparatus 100 to plot the slope of a straight line between point (0, 0) and (X, Y). FIG. 5 is a graphical representation of a solids contaminant loading curve for a filter. As can be seen, increasing slope (m) values from the baseline, will indicate higher pipeline solid contaminants loading, which correlates to a decrease in time between two pressure drops and an increase in the pipeline solid contaminant concentration level.

A decrease in the time between set differential pressure points corresponds to a higher slope value, and can be used to calculate the contaminant concentration level in the pipeline. As referenced above, these concentration values may also be evaluated and illustrated as possible alarm lines on a web-based end user page on the system server. The slope from the line, Y=mX, in FIG. 4 uses the laboratory test data and the operations time values so that the concentration of solids can be measured.

In certain embodiments, the processor 124 is configured to determine variances of the solid contaminant concentration level in the pipeline based on pressure-sensor measurements corresponding to specific differential pressure drops. One method for making this determination involves using a simple linear regression analysis. This method uses the least squares model to correlate the real time data, logged to the data history, so that a variance from the average solid contaminant concentration level can be calculated.

In certain embodiments, the processor 124 records the pressure differential across the filter element 103 at regular time intervals. The processor 124 determines a level of solid contaminant concentration in the gas stream based upon a rate of change of the sensed pressure drop in comparison to pressure drop versus time data for an empirically-determined baseline contaminant loading of a filter.

More specifically, this method calculates the best fit of all collected data points. Using linear regression allows the processor 124, or server, to calculate a line that will minimize the variance in the data points and calculate $R^2$ (R squared). $R^2$ is a statistical measure for goodness-of-fit so that data points outside of $R^2$, for real time data, can be measured to a statistical confidence range. In particular embodiments, the new data can then be illustrated on a chart as an alarm trend line, and displayed on the aforementioned end user web page. Variances above a predetermined threshold could automatically trigger visual or audible alarms.

Referring again to FIGS. 1 and 2, embodiments of the pipeline contaminant monitoring apparatus 100 are also configured to measure a liquid contaminant concentration level in the pipeline gas stream. As will be explained in more detail below, the contaminant monitoring apparatus 100 may be configured to collect, from the filter barrier, liquid contaminants in a collection chamber 128, which may be attached to the filter housing 102. The contaminant monitoring apparatus 100 records the time required to collect a predefined amount of liquid contaminants in the collection chamber 128, and determines a liquid contaminant concentration level in the pipeline gas stream based on the time required to collect the predefined amount of liquid contaminants.

Liquid droplets will be coalesced by the filter element 103 and will migrate down the outside of the filter element 103 by gravity. The droplets will continue to collect on the outside of the filter 103 until heavy enough to drop from the filter 103 to the inside of the housing 102. The bottom of the filter housing 102 is shaped such that the droplets will then drain from the filter housing 102 to the liquid collection chamber 128. Typical filter housings 102 range from 1.5 inches to 6 inches in diameter, depending on the amount of sample gas needed and the expected normal concentration of solids in the gas stream. In certain embodiments, the filter housing 102 is attached at a bottom portion to the liquid collection chamber 128. In some embodiments, a pipe connection will allow pressure equalization and liquid drainage between the filter housing 102 and the liquid collection chamber 128. Liquids that drain from the filter element 103 will drain to the bottom of the filter housing 102 and will continue draining by gravity to enter and come to rest in the liquid collection chamber 128.

In certain embodiments, the liquid collection chamber 128 will have a float-type level switch 132 or like device that will send an electric signal to the processor 124 via the RTU 122 when a known volume of liquid is collected. Once enough liquid has been captured in the liquid collection chamber 128 to raise the float and trip the level switch 132, a signal will be sent by the RTU 122 to the processor 124 or server. In some embodiments, the processor 124 compares the known amount of liquid collected, i.e., the amount required to trip the level switch 132, with the time required to collect the liquid, and the flowrate through the pipeline 104, in order to produce a liquid contaminant concentration level for the gas stream over a period of time.

The liquid collection chamber 128 may also include a drain valve 134 for emptying and sampling the liquid collection chamber 128 after the float-type level switch 132 has been activated.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A pipeline contaminant monitoring apparatus comprising:
    i) a filter housing and a sampling probe configured to isokinetically sample a portion of a pipeline gas stream, the filter housing having a filter configured to trap solid contaminants within the gas stream;
    ii) a first pressure sensor located upstream of the filter and a second pressure sensor located downstream of the filter; and
    iii) a processor coupled to the first and second pressure sensors, the processor configured to determine a solid contaminant concentration level in the gas stream based on a rate of change of the pressure drop sensed across the filter;
        wherein the processor is configured to compare the pressure drop sensed across the filter to empirically-derived data for contaminant concentration, the comparison resulting in a real-time determination of solid contamination concentration in the pipeline gas stream, based on a scaling of a mass of solids, measured at two different differential pressures, in the pipeline filter; and
    further comprising a liquid collection chamber attached to a gravitational bottom of the filter housing, the liquid collection chamber positioned to collect liquid droplets from the filter,
    iv) wherein the liquid collection chamber includes a float switch configured to generate an electrical signal when a predefined amount of liquid is collected in the liquid collection chamber; and
    v) wherein the processor is configured to determine a level of liquid contaminant concentration in the gas stream based on a time required for the float switch to generate the electrical signal.

2. The pipeline contaminant monitoring apparatus of claim 1, further comprising a remote transmitting unit (RTU) configured to transmit data signals from the first and second pressure sensors to the processor.

3. The pipeline contaminant monitoring apparatus of claim 2, wherein the processor is remotely located from the first and second pressure sensors.

4. The pipeline contaminant monitoring apparatus of claim 2, wherein the remote transmitting unit (RTU) is configured to wirelessly transmit data signals from the first and second pressure sensors to the processor.

5. The pipeline contaminant monitoring apparatus of claim 1, wherein the sampling probe is positioned to isokinetically divert a portion of the gas stream from the pipeline to the filter housing.

6. The pipeline contaminant monitoring apparatus of claim 1, wherein the processor is configured to generate an alarm if the solid or liquid contaminant concentration level is higher than a threshold level.

7. The pipeline contaminant monitoring apparatus of claim 1, further comprising a booster pump to inject the sampled portion of the pipeline gas stream back into the pipeline gas stream.

8. A method of monitoring contaminant concentration in a pipeline gas stream, the method comprising the steps of:
    i) diverting a portion of a pipeline gas stream and directing the diverted portion of the gas stream through a filter barrier;
    ii) measuring a pressure differential across a filter barrier at a first time, and measuring the pressure differential across the filter barrier at a second time later than the first time, and determining a measured rate of change for the pressure differential over a time period from the first time to the second time;
    iii) storing empirical data for solid contaminant concentration with respect to a differential pressure rate of change across a filter medium;
    iv) comparing the measured rate of change in the pressure differential to the empirical data;
    v) determining a solid contaminant concentration level based on the comparison, wherein determining a solid contaminant concentration level comprises:
    scaling the empirical data to account for an inner diameter of the pipeline; and
    using the time period to determine the solid contaminant concentration level for a standard gas flowrate through the pipeline.

9. The method of claim 8, further comprising:
    i) collecting, from the filter barrier, liquid contaminants in a collection chamber;

ii) determining a time for collecting a predefined amount of liquid contaminants in the collection chamber; and, iii) determining a liquid contaminant concentration level in the pipeline gas stream based on the time required to collect the predefined amount of liquid contaminants.

10. The method of claim 9, further comprising generating an alarm if the solid or liquid contaminant concentration level is higher than a threshold level.

11. The method of claim 8, further comprising displaying the contaminant concentration level on an electronic display.

12. The method of claim 8, further comprising transmitting pressure differential data to a remotely-located processor that determines the measured rate of pressure change, stores the empirical data, and compares the measured rate of pressure change to the empirical data.

13. The method of claim 8, wherein diverting a portion of the pipeline gas stream comprises inserting a probe into the pipeline, the probe configured to isokinetically sample the portion of the pipeline gas stream.

14. The method of claim 8, further comprising injecting the diverted portion of the gas stream back into the pipeline.

\* \* \* \* \*